United States Patent [19]

Saunders

[11] Patent Number: 5,649,659
[45] Date of Patent: Jul. 22, 1997

[54] DISPENSING MEANS

[75] Inventor: Stuart David Saunders, Murwillumbah, Australia

[73] Assignee: Esfloss (H.K.) Ltd., Hong Kong

[21] Appl. No.: 691,440

[22] Filed: Aug. 2, 1996

Related U.S. Application Data

[63] Continuation of Ser. No. 204,154, filed as PCT/AU92/00466, Sep. 2, 1992, published as WO93/04640, Mar. 18, 1993, abandoned.

[30] Foreign Application Priority Data

Sep. 2, 1991 [AU] Australia ................ PK8077
Jul. 29, 1992 [AU] Australia ................ PL3796

[51] Int. Cl.$^6$ .................................. A61C 15/04
[52] U.S. Cl. .................. 225/39; 132/325; 225/56
[58] Field of Search ................ 225/39, 46, 77, 225/56, 47; 132/324, 325; 206/63.5

[56] References Cited

U.S. PATENT DOCUMENTS

| | | | |
|---|---|---|---|
| 1,233,687 | 7/1917 | Muchow | 132/325 |
| 2,893,405 | 7/1959 | Castelli . | |
| 4,004,599 | 1/1977 | Rosenfeld | 132/325 |
| 4,019,522 | 4/1977 | Elbreder . | |
| 4,327,755 | 5/1982 | Endelson . | |
| 4,881,560 | 11/1989 | Blank et al. . | |
| 4,934,389 | 6/1990 | Pettiford | 132/325 |
| 5,054,674 | 10/1991 | Fortman | 225/77 |
| 5,065,861 | 11/1991 | Greene et al. . | |
| 5,076,423 | 12/1991 | Russack . | |
| 5,495,863 | 3/1996 | Bergman | 132/326 |
| 5,524,764 | 6/1996 | Kaufman et al. | 206/581 |

FOREIGN PATENT DOCUMENTS

| | | |
|---|---|---|
| 82290 | 10/1983 | Australia . |
| 66750 | 6/1989 | Australia . |
| 76276 | 3/1992 | Australia . |

*Primary Examiner*—Kenneth E. Peterson
*Attorney, Agent, or Firm*—Sughrue, Mion, Zinn, Macpeak & Seas

[57] ABSTRACT

A credit card size dispenser (10) is provided which is particularly suited for dispensing dental floss. The dispenser (10) includes a thin rectangular housing (11) which supports a spool of floss (12) wound in an oval form to provide an elongated open centre portion (13) into which floss may be drawn from the inner end of the spool (12). One major face of the housing contains an elongate recess (14) which extends into the elongated open centre portion (13). This recess (14) contains, at a level below the major face, a floss lead-out guide (16) at one end and at the other end a severing device (18). The exposed lead-out portion (21) of the floss which extends between the lead-out guide (16) and the severing device (18) is also held below the major face whereby the dispenser (10) has no external protuberances to snag adjacent items.

7 Claims, 4 Drawing Sheets

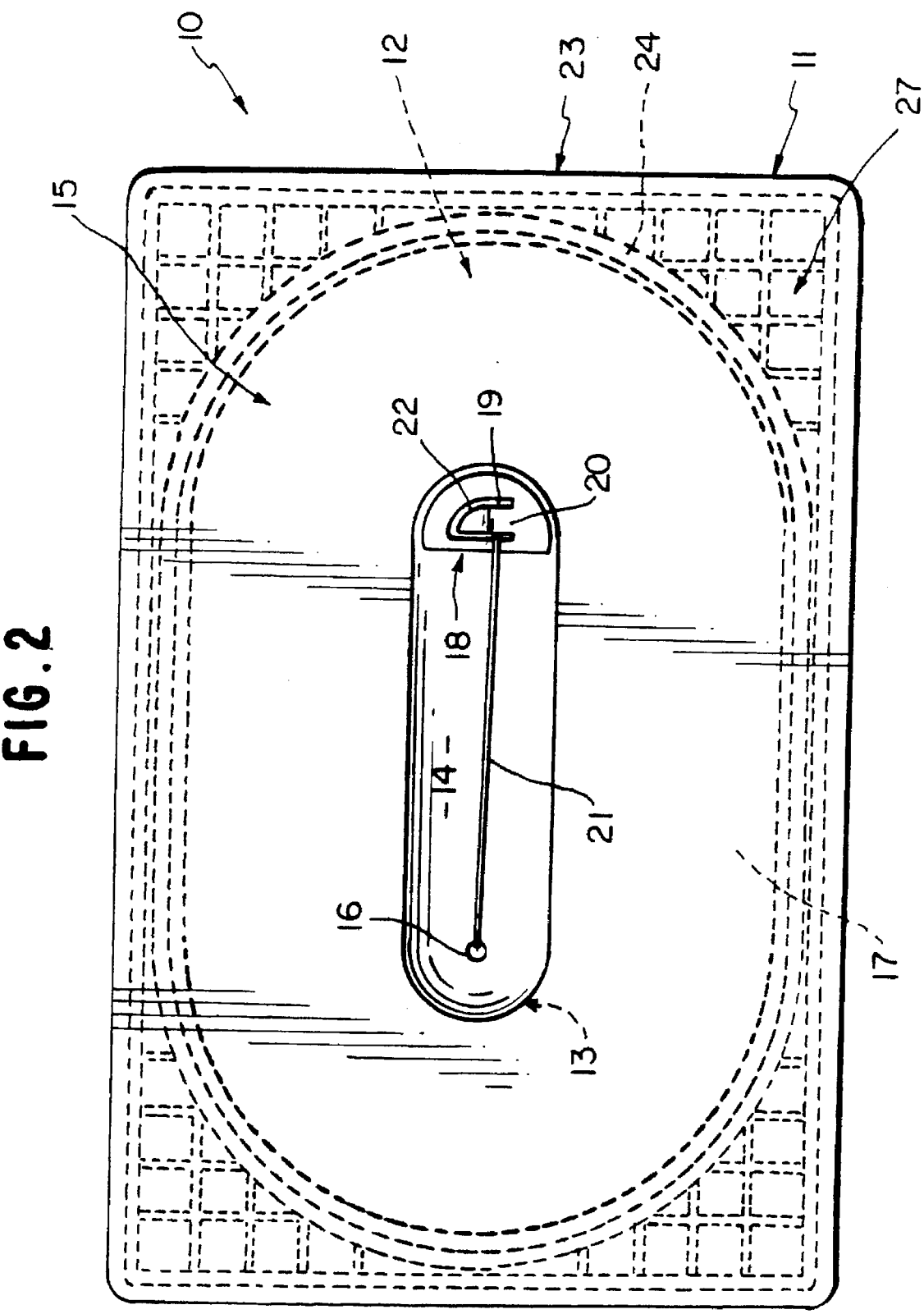

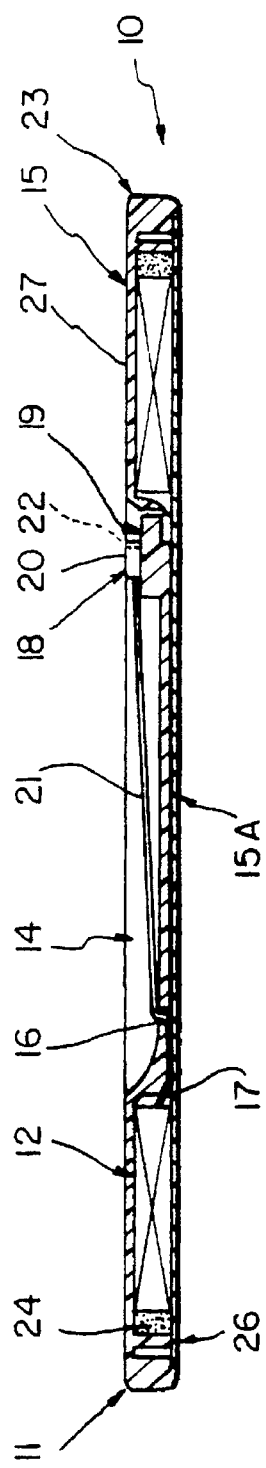
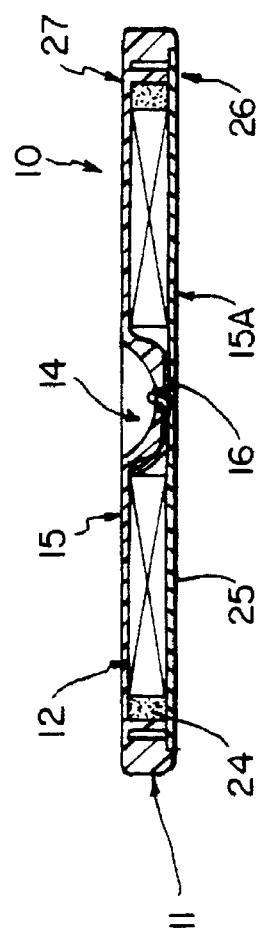
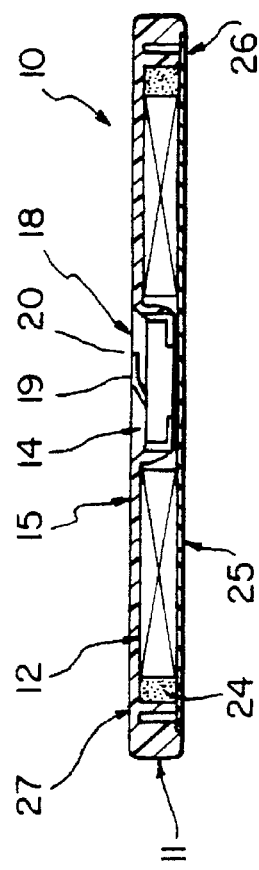

DISPENSING MEANS

This is a continuation of application Ser. No. 08/204,154, filed as PCT/AU92/00466, Sep. 2, 1992, published as WO93/04640, Mar. 18, 1993, now abandoned.

This invention relates to thread dispensing means.

This invention has particular reference to dispensing means for dispensing dental floss and for illustrative purposes particular reference will be made hereinafter to such application. However it is to be understood that this invention can be used for dispensing other forms of threads and filaments such as, for example, fuse wire or sewing, binding or whipping thread, tie wire or fishing line.

Many advances have been made in recent years in dental health and hygiene. These have ranged from treatment of reticulated water supplies with fluoride to considerably reduce incidence of cavities in the teeth of the population, to new materials for repair of damaged teeth, and new methods of diagnosis and treatment for all problems of the teeth and mouth. A plethora of devices ranging from the traditional tooth brush, geometric tooth brushes rotating head tooth brushes, water jet tooth brushes, tooth picks, flosses and floss/tooth pick combinations supplement the above advances in dental health, making a high level of oral hygiene possible.

Many companies around the world manufacture dental floss dispensers. Typically such floss dispensers are formed as rectangular packages about 20 mm thick, 40–60 mm wide, and 55–70 mm high. However, while the advantages of using dental floss after each meal are well recognised, the present inconvenience of use resulting from the relatively bulky packages deters such use.

This invention aims to alleviate at least one of the abovementioned disadvantages and to provide thread dispensing means which will be reliable and efficient in use. Other advantages of this invention will hereinafter become apparent.

With the foregoing and other objects in view, this invention in one aspect resides broadly in thread dispensing means including:

supporting wall assembly;

a thread guide in the supporting wall assembly;

a spool of thread from which the lead-out portion of the thread may be dispensed to a fixed location without passing across the spool, said spool being fixedly supported by said wall assembly with said thread passing to said thread guide and said thread guide being disposed whereby said lead-out portion of the thread may feed thereto without passing across the spool.

The spool of thread may be a coil of thread and the lead out portion of the thread may lead from the inner end of the spool whereby it may be dispensed to a fixed location within the centre of the spool without passing across the spool. Alternatively, the spool may be of the type in which the thread is built up in a concertina or fan-folded arrangement and the lead-out portion of the thread may lead from one end of the spool whereby it may be dispensed to a fixed location at the side of said lead-out portion remote from the spool and without passing across the spool.

Suitably the thread guide is arranged in a wall portion of the wall assembly which is recessed below the adjacent face of the spool. The recessed wall portion may also support severing means for severing thread dispensed through the thread guide.

In a preferred embodiment of the invention the dispensing means is adapted as a dental floss dispenser and the spool of dental floss is formed as a very narrow spool whereby the thickness of the dispensing means may be minimised. Suitably the dispensing means is thin and has major face dimension similar to a credit card whereby it may be supported in a wallet.

In a further aspect this invention resides broadly in dental floss dispensing means including:

supporting wall assembly having exterior dimensions similar to a credit card whereby the dental floss dispensing means may be supported in a wallet;

a spool of floss supported within said supporting wall assembly;

a floss guide in the supporting wall assembly through which the lead-out portion of the floss may be dispensed, and severing means for severing floss dispensed through the thread guide.

Preferably the floss guide and the severing means are arranged in a wall portion of the wall assembly which is recessed below the adjacent face of the floss spool. The spool may be rotatably supported in the wall assembly to facilitate dispensing of floss therefrom. Preferably however the floss is non-rotatably supported within the wall assembly, the spool is in the form of a coil of floss from which the lead-out portion leads from the inner end of the coil and the recessed wall portion extends into the open centre portion of the coil.

Preferably the spool of thread or floss is wound on a suitable former, preferably using waxed or other coated thread or floss whereby the thread or floss has the ability to cohere, thus giving adequate inherent structural strength whereby it may be removed from the former, and fixedly supported between thin shell-like walls spaced apart by the thickness of the spool. For example a plastisol or other plastic coating, such as is used in unwaxed dental floss may be used. Impregnation of tile yarn with wax or other suitable material, which undergoes phase change or solidification after the spool is wound, imparts structural strength to the spool.

Suitably the spool of thread or floss is formed as a thin ovoid shaped spool whereby a longitudinal protuberance may be formed in the wall assembly extending into the centre portion of the spool and forming an external recess so as to accommodate the thread guide at one end and the severing means at the other end, leaving sufficient space therebetween to enable a user to gain finger access to the thread extending between the thread guide and the severing means. Preferably the thread guide at one end of the recess is disposed at a lower level than the severing means at the other end whereby floss may be pulled from the thread guide and engaged with the severing means without having to manipulate the thread intermediate the thread guide and the severing means. It is also preferred that the thread guide, the severing means aperture and the thread extending therebetween all lie below the top or outer major face of the supporting wall assembly and between the Opposed major faces of the wall assembly.

The spool may be formed by winding on a shaped formed, held between two plates spaced appropriately to control the thickness of the spool of floss or thread or filament or the like and hereinafter collectively referred to as floss. During winding, application of heat may be useful to melt or soften the wax or other coating on the floss and this coupled with the tension of the thread or floss caused the spool to fuse into the integral formerless spool required.

The flat spool of floss with an elongated hole in the centre provides for a minimum thickness package which is further assisted by forming the recess for the guide means, the severing means and for the floss to pass therebetween, all within the spool centre cavity. Thus all major elements lie substantially within the same plane. As the guide means and cutter are within the centre of the spool of floss, when the floss is drawn from the dispensing means it is drawn from the inside of the spool. Thus the floss can unwind without the spool rotating or moving and also with a minimum of twisting. Thus the floss as it comes out is substantially straight because the inner circumference of the spool at all times, is relatively large compared to conventional spools of floss packages. For example in a credit card size dispensing means the minimum inner circumference of the spool is in the order of 110 millimeters and increases as the floss is used. Thus the undesirable tendency that conventional flosses have of twisting after cutting may be reduced.

Alternatively the floss may be wound as a cylinder having a circumference slightly less than one half of the major dimensions of the final package, and the length of the cylinder being slightly less than the other major dimension of the package. After winding, the cylinder is then flattened to form a rectangle. The floss may also be wound flat directly. Each final dimension would be less than the internal dimension of the housing to allow for clearance between the floss and the housing. This clearance can be minimal, as the spool may be fixedly mounted in the housing. The thickness of the cylinder would be one half the thickness of the required floss package (say 1.3 millimeters) so that on flattening the cylinder, package of the required thickness (say 2.6 millimeters not including wall thickness) would be produced.

It is also preferred that the lead-out portion of the floss which remains in the package is retained by the severing means. This may be achieved by forming the cutting member of the severing means with a cutting edge distant from the guide means and a retaining edge adjacent the guide means. Furthermore with the floss guide means and the severing means recessed in the centre of the side wall face, the floss line may be maintained below the adjacent major surface of the housing, even when cutting. Thus the floss will tend to stay cleaner. Also, the cutter of the severing means will not be prone to catch on clothes or to injure, as its top surface need not protrude beyond the adjacent major surface of the housing.

In order to prevent the spool from collapsing when the last few coils of floss remain, the outer surface of the spool is bonded into the housing so that it is supported against collapse even when just a little floss remains.

Accordingly in another aspect, this invention resides in a method of supporting a spool of thread to be dispensed in a housing including:

inserting the spool into the housing, and encapsulating the spool within the housing with a suitable medium which does not prevent withdrawal of the thread from the spool. Preferably the medium is wax. This may be introduced by clamping the spool between a side wall of the housing and a false back wall so as to form an airtight chamber containing the spool. Molten wax is drawn into this airtight chamber through one hole in the false back wall, connected to a supply of molten wax, by applying a vacuum to another hole in the false back. Typically these holes would be at opposite ends of the chamber, and the hole to which the vacuum is applied could be elevated relative to the other hole, so that a "bleed" effect ensures that all air bubbles are removed. The wax may be circulated through both holes in normal operation, ie. injecting the wax, and short circuited through the controlling valve when not operating. This will ensure that the wax remains molten at all tames. Continuous circulation will prevent "freezing" of the wax in the valve rendering the valve inoperable during the production process.

In order that this invention may be more readily understood and put into practical effect, reference will now be made to the accompanying drawings which illustrate preferred embodiments of this invention and wherein:

FIG. 2 is a diagrammatic plan view illustrating the layout of the dispenser illustrated in FIG. 1;

FIG. 3 is a sectional view through the longitudinal centreline of the dispenser;

FIGS. 4 and 5 are respective transverse sectional views through the floss lead out guide and the floss severing means.

Figure 1:
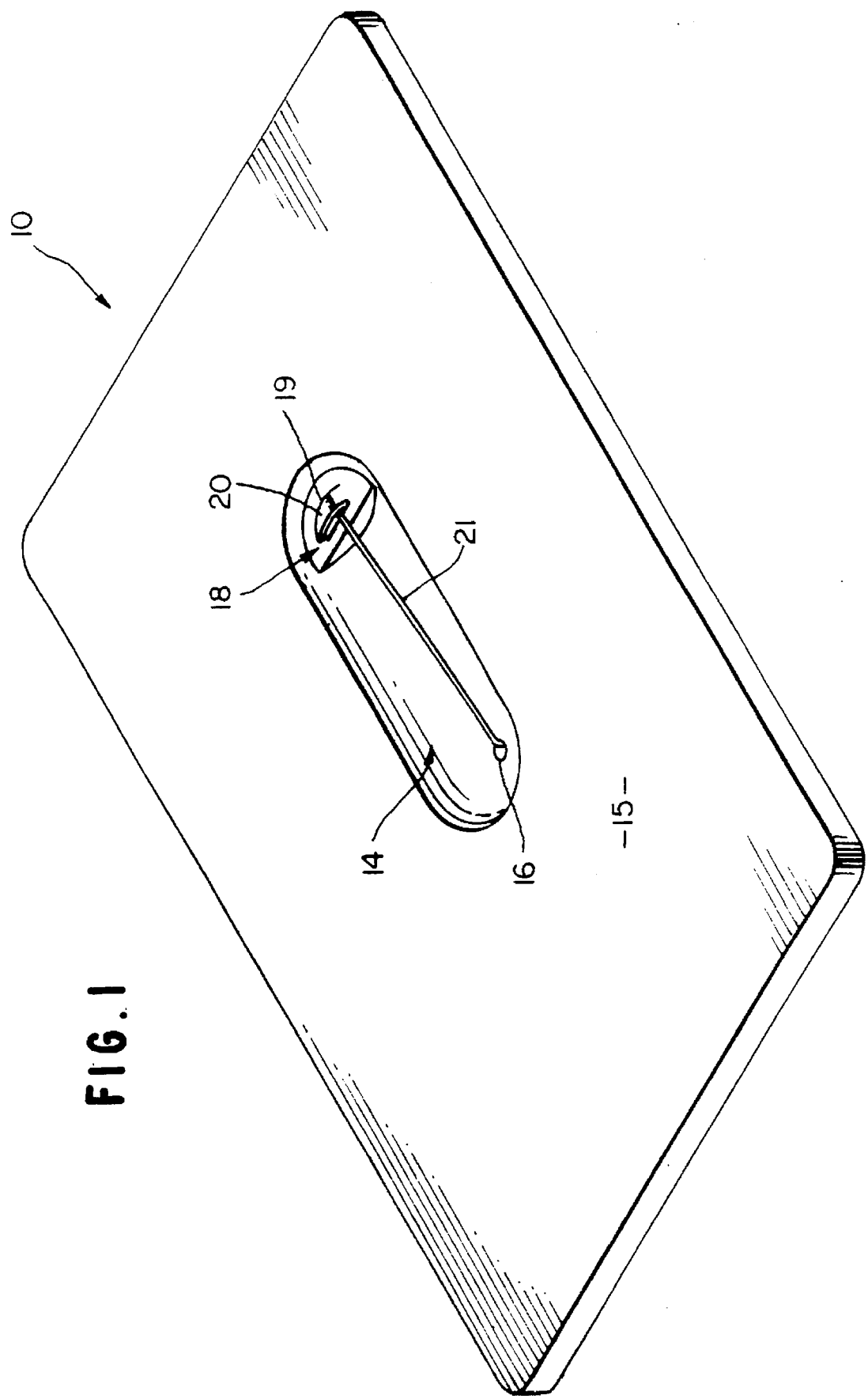
FIG. 1 is a perspective view of a preferred form of dental floss dispenser.

The dental floss dispenser 10 illustrated in FIG. 1 is o substantially credit card size, which is an acceptable size for consumers, being able to fit easily and unobtrusively into a standard wallet or pocket. The external housing 11 is formed of a plastics material and has major face dimensions of 86 mm×54 mm and a thickness of approximately 3.6 mm. The housing 11 contains approximately 50 meters of dental floss stored internal thereof in a oval shaped spool 12 as can be seen from FIG. 2. The spool 12 is relatively thin and is formed with a relatively large open centre 13 which is elongated.

An elongated external recess 14 is formed in one side wall 15 of the housing 11 in an inwardly extending protuberance and supports, at one end, a lead out aperture 16 through which the floss 17 is dispensed from the interior of the spool 12. The recessed side wall 15 is disposed parallel to the major faces of the spool and the recess 14 extends into the large open centre 13 of the spool 12 and terminates in spaced relationship with the opposite planar side wall 15a. The recess 14 is relatively deep adjacent the aperture 16 and continues along at this depth to its opposite end at which the thread cutter/holder 18 is disposed above the base of the recess 14. The cutter/holder or severing means 18 is formed from stainless steel and includes a raised tongue portion 20 struck from the thread cutter 28. The tongue 20 is raised slightly and extends substantially in the same plane as the planar portion of the side wall 15. The tongue 20 forms a cutting edge 19 adjacent the end of the recess 14. The cutting edge is formed with an inwardly sloping chamfer 22 in order to minimise risk of personal injury.

A lead of floss 21 stretches from the aperture 16 to the raised tongue 20 at which it is held. The lead of floss extends along the recess 14, below the level of the planar portion of the side wall 15 and above the base of the recess whereby it spans between the aperture 16 and the tongue 20 in free space making it easily accessible for grasping.

The floss spool 12 is non-rotatably supported between the side walls about the protuberance and unwinds from the inside of the spool whereby the lead-out floss 21 passes from the inner face of the spool and out through the aperture 16 to the recess 14. Sufficient spacing exists between the aperture 16 and the cutter 18 to allow a user's finger to grasp the lead of floss 21 and to draw it through the aperture 16. Floss drawn therefrom unwinds from the inside of the spool, while the body of the spool remains fixed and stationary within the housing.

In a typical use, the floss dispenser 10 is held horizontally by its long sides between the thumb and forefinger of the left hand. The user, after grasping the lead of floss 21 and pulling out the required amount of floss then wipes the floss along the edge 23 of the housing 11 adjacent the three cutter 18. The location of the floss exit aperture 16 in the base of the recess 14 causes such wiping action to initially engage the floss under the tongue 20 for clamping thereby and s the user draws the floss further along the edge 23 the floss will be severed by the cutting edge 19. After cutting, the end of the floss remains attached to the spool inside the housing 11 and is retained under the tongue 20 providing a new lead of floss 21 ready for further dispensing. The cutting action occurs even though the cutting edge 19 is entirely below the top surface of the housing because of the relatively lower location of the aperture 16.

The above arrangement ensures maximum safety and also obviates the need for a safety cover. This safety is further enhanced by the chamfered configuration of the cutting edge 19 which prevents the skin being caught under the cutting edge 19, thereby preventing injury. This safety design alleviates damage to clothing and the like.

The spool 12 is secured within the housing 11 by solidified wax, 24 or other suitable material. This body of wax fixes the spool within the housing, and prevents collapsed of the spool when only a few threads remain. A back plate 25 forms the back surface of the housing 11 and is joined at 26 to the front wall assembly 27 by suitable means such as ultrasonic welding or solvent welding, or by adhesive bonding.

The above arrangement is very efficacious to use. An advantage of the particular arrangement is that the opposed flat surfaces of the housing 11 can be used for product or company information, advertising or other promotional information, reproduction of paintings or photographs, information such as dentist's appointment reminders and contact details, or user and community medical information such as blood group, allergies and/or other special medical conditions, whether organ donations are permitted, etc.

This design is also relatively rigid for a thin assembly

The strength is a result of the physical arrangement of the elements which is that of an entirely closed rectangular prism with only one aperture near the centre and recess, the location and shape of which acts as a spacer to keep the walls apart under bending or torsion, maintaining its strength.

A preferred method for assembling the dental floss dispenser 10 is as follows. An appropriate floss fibre is selected which is coated with wax or with another suitable material. The floss is then heated to melt the coating, and is then wound on a mandrel which has a suitably shaped core to produce the required elongated hole in the centre of the finished spool. The circumference of the core may require a relief angle e.g. 45 degrees to facilitate release of the spool from the mandrel. When the mandrel is unclamped, the tension within the spool, and the stretch of the floss will cause the spool to slide down the 45 degree slope, automatically releasing itself from the core and one side, to remain loosely attached to the other side which is flat.

The core is located in the mandrel between a pair of parallel plates which are spaced apart by an amount equal to the thickness required for the finished spool. Typically, this thickness, or the distance between the plates, will be established by the thickness of the core. In operation, the lead-out end of the floss is secured between the core and one of the side plates, and the entire assembly is placed in sufficient axial compression to prevent the plates moving apart as the floss builds up, and the total tension in the spool increases. This compression may be provided by a bolt and nut or by a clamping mechanism. The floss is passed through a wax bath, and/or tensioning devices as required. It may be then passed through a hot air blast which melts the wax on the floss and controls the temperature of the floss as it is wound. The mandrel may be preheated or precooled, if necessary, according to the coating material and other characteristics of the materials used. It is considered that preheating should maintain the desirable wax coating on the floss where wax coating is utilized. The mandrel is rotated at an appropriate speed and the floss is wound on. As the wax cools, it fuses together imparting solidity to the spool. After cooling, the spool is released from the mandrel.

The cutter is inserted into the housing and secured, preferably by clinching. The housing is then placed on the assembly table. Alternatively, the cutter may be inserted by injection of the plastic of the housing around the cutter which has been previously placed in the injection mould. When the housing is placed on the assembly table a vacuum, ducted through the table, may be used to clamp the housing onto the table. The spool is then placed into the housing. The vacuum may then be used to suck the lead-in end of the floss through the thread guide or thread exit hole.

When the spool is correctly located, a false back which consists of a flat piece of rigid material, preferably transparent, and which has a thickness of a soft material such as polyurethane or silicone rubber, preferably also transparent, is placed on top of the housing and spool. The soft material produces a good seal, and the clamping pressure of the vacuum means that it also protrudes into the cavity, ensuring that the wax cast has a concave top surface. This facilitates the attachment of the backplate by maintaining the wax clear of the weld area ensuring good bonds. The vacuum holding the housing to the assembly table is then transferred, via the floss exit hole, to the centre of the false back. The vacuum then clamps the false back to the housing. The false back seals a cavity between itself, the outside of the spool and the inside of the housing. A pair of holes in the false back provide access to diametrically opposite points of the cavity. A vacuum is applied to one of these holes, and the other hole is connected to a supply of molten wax. The wax is then sucked into one hole and then passes out via the other hole. Alternatively, molten wax or other material can be pumped in via one hole and bled out via the other hole, in a similar manner. The valve controlling the flow of wax will ideally continually circulate the hot wax when not "injecting" to prevent the wax from freezing.

After an appropriate time, i.e. when the air is bled out, and the heat of the molten wax has created a good bond to the spool and to the housing, the vacuum or wax supply is cut off and the assembly is allowed to cool. When the wax has solidified, the vacuum is released, and the false back is removed and the back plate is placed on the housing. The backplate may also be secured by vacuum which may be a different level of vacuum to that used for securing the back plate. The back plate is welded to the housing by an ultrasonic welder, or by solvent welding or adhesive bonding. Assembly is now completed and the product can be released from the assembly table, by terminating the vacuum.

Figures 6, 7, 8:
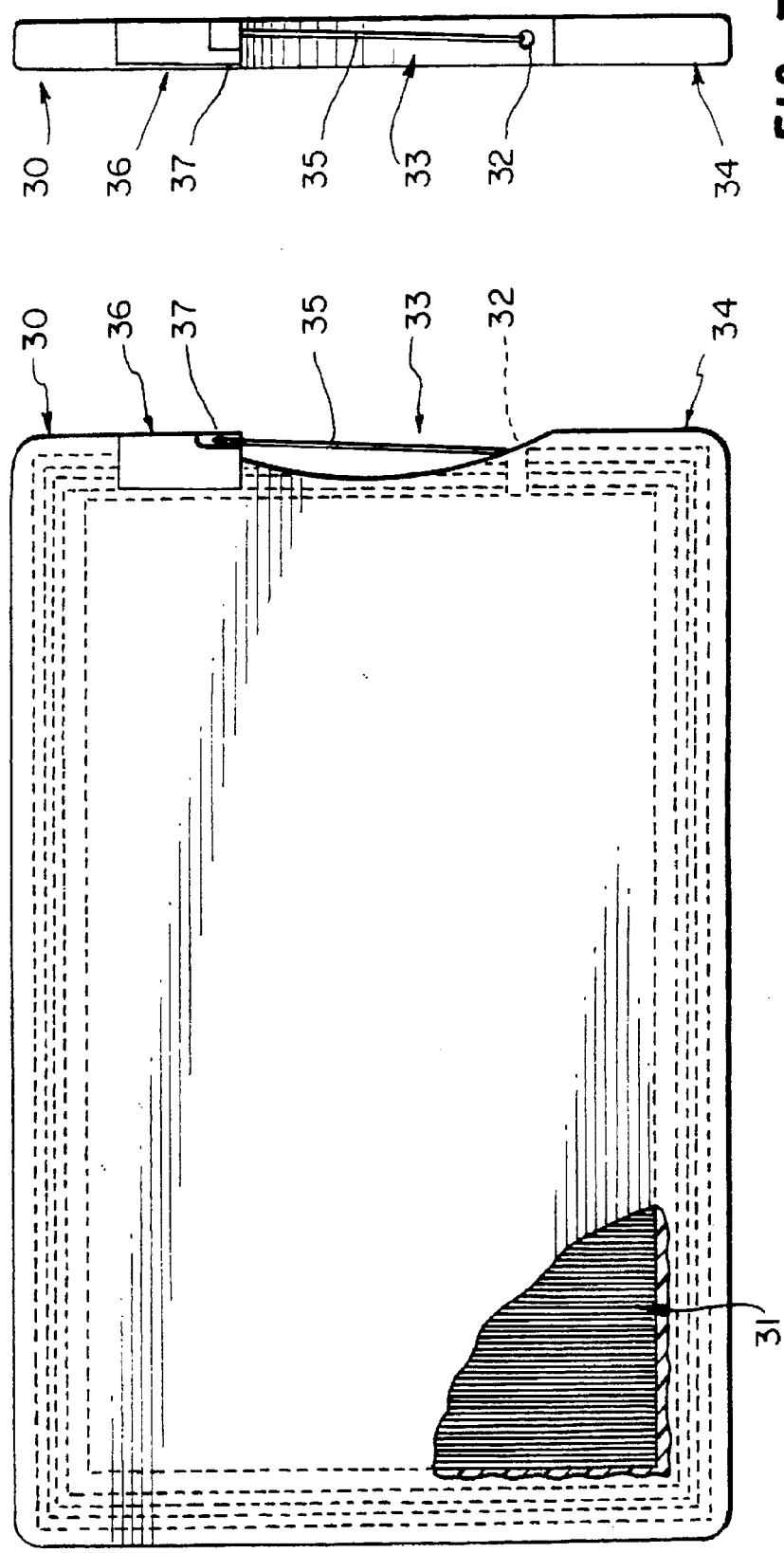
FIGS. 6, 7 and 8 illustrate a further embodiment of the invention.

The floss dispenser 30 illustrated in FIGS. 6 to 8 utilises a fan-folded spool of floss 31 of rectangular configuration from which the floss is dispensed from one end through a aperture 32 in the dished top end 33 of the housing 34. The lead-out floss 35 extends accessibly in free space across the dished end 33 to a metal cutter assembly 36 mounted at the remote end of the dished end 33. The cutter assembly 36 incorporates a cutting tongue 37 against which the floss may be severed and beneath which the lead-out floss 35 is retained.

It will of course be understood that the above has been given by way of illustrated example only and all such modification and variations thereto as would be apparent persons skilled in the art are deemed to fall within the broad scope and ambit of the present invention as defined in the appended claims.

What we claimed is:

1. Dispensing apparatus for dispensing dental floss including:

a housing having two spaced apart wall portions;

a protuberance extending inwardly from one wall portion substantially centrally thereof and terminating in a base portion disposed in closely spaced proximity to said other wall portion, said protuberance defining a recess in said one wall portion;

a spool of floss in the form of a substantially planar oval shaped ring non-rotatably supported between said wall portions about said protuberance, said spool including a continuous spiral wound floss having an inner end and an outer end, and means for preventing rotation of said spool about said protuberance;

an aperture extending through said one wall portion into said recess to form a floss guide through which the inner end of said floss may be drawn, and severing means for selectively severing floss drawn through said floss guide, said severing means being disposed within said recess.

2. Dispensing means as claimed in claim 1, wherein adjacent windings of said floss are bonded to one another.

3. Dispensing means as claimed in claim 2, wherein said severing means retains floss which extends from said floss guide to said severing means.

4. Dispensing means for dispensing dental floss as claimed in claim 3, wherein floss retained between said floss guide and said severing means is retained within said recess.

5. Dispensing means as claimed in claim 4, wherein said housing is substantially rectangular with a low side and has exterior dimensions similar to a credit card.

6. Dispensing apparatus as claimed in claim 5, wherein said recess is a substantially oval shaped recess having a major axis parallel to or coincident with the long side of said housing.

7. Dispensing means as claimed in claim 4, wherein said spool of floss is bounded by a solidified material which cooperates with one of said wall portions to prevent rotation of said spool.

* * * * *